United States Patent
Farrand et al.

(10) Patent No.: US 6,939,479 B2
(45) Date of Patent: Sep. 6, 2005

(54) CYCLOALKANONE DERIVATIVES

(75) Inventors: Louise Diane Farrand, Manchester (GB); Christopher Worrall, Northwich (GB); Owain Llyr Parri, Dorset (GB); Ian Victor Edward Hassall, Ringwood (GB); Julian Frederick Samuel Vaughan-Spickers, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 285 days.

(21) Appl. No.: 10/116,745

(22) Filed: Apr. 5, 2002

(65) Prior Publication Data

US 2003/0080321 A1 May 1, 2003

(30) Foreign Application Priority Data

Apr. 6, 2001 (EP) .............................................. 01108721

(51) Int. Cl.$^7$ .............................................. C09K 19/52
(52) U.S. Cl. ........................... 252/299.63; 252/299.61; 252/299.01; 568/303; 568/367
(58) Field of Search ........................ 252/299.01, 299.2, 252/299.3, 299.6, 299.61, 294.63, 299.64, 299.65, 299.66, 299.67, 299.68, 299.7, 299.63; 428/1.1, 1.2, 1.25, 1.26; 585/25, 26; 568/303, 367, 563, 607

(56) References Cited

U.S. PATENT DOCUMENTS

| 5,250,735 | A | * | 10/1993 | Wong et al. ................. 564/442 |
| 5,886,232 | A | * | 3/1999 | Landscheidt et al. ....... 568/322 |
| 6,215,028 | B1 | * | 4/2001 | Oster et al. ................. 568/362 |
| 6,448,220 | B1 | * | 9/2002 | Swift ........................... 512/23 |
| 6,541,672 | B1 | * | 4/2003 | Sardjiman et al. .......... 568/308 |

FOREIGN PATENT DOCUMENTS

| DE | 44 05 316 | * | 8/1995 | ......... C07C/69/773 |
| JP | 01-312550 | * | 12/1989 | ............ G03G/5/06 |

OTHER PUBLICATIONS

Derwent English language abstracts supplied for both references.*

* cited by examiner

Primary Examiner—Mark F. Huff
Assistant Examiner—Jennifer R. Sadula
(74) Attorney, Agent, or Firm—Millen, White, Zelano, Branigan, P.C.

(57) ABSTRACT

Described herein are compounds of formula I

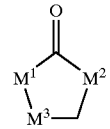

I wherein $M^1$, $M^2$ and $M^3$ have the meanings recited in the disclosure, liquid crystalline mixtures and polymers containing them, and the use of the compounds of formula I, the liquid crystalline mixtures and the polymers containing them in optical and electrooptical devices like liquid crystal displays or projection systems, patterned films and optical elements like polarizers, retardation films, compensators, color filters, holographic elements or polarization beam splitters, for photoswitching, in anisotropic membranes for the permeation of gases or fluids, adhesives, synthetic resins with anisotropic mechanical properties, cosmetic or pharmaceutical compositions, UV absorbers and sunscreens, diagnostics or liquid crystal pigments, for decorative and security applications, in nonlinear optics, optical information storage or as dopants.

30 Claims, No Drawings

CYCLOALKANONE DERIVATIVES

FIELD OF THE INVENTION

The invention includes to novel cycloalkanone derivatives, liquid crystalline mixtures and polymers containing them, and use of the novel compounds, mixtures and polymers in optical and electrooptical devices like liquid crystal displays or projection systems, patterned films and optical elements like polarizers, retardation films, compensators, color filters, holographic elements or polarization beam splitters, for photoswitching, in anisotropic membranes for the permeation of gases or fluids, adhesives, synthetic resins with anisotropic mechanical properties, cosmetic or pharmaceutical compositions, UV absorbers and sunscreens, diagnostics or liquid crystal pigments, for decorative and security applications, in nonlinear optics, optical information storage or as dopants.

BACKGROUND OF THE INVENTION

Photoisomerizable mesogenic molecules which change their shape on photo-irradiation ae known in prior art. When irradiated e.g. with UV light, they show E-Z or cis-trans isomerization.

Photoisomerizable compounds that are mesogenic, i.e. exhibit or induce liquid crystal phase behavior, can be used inter alia to prepare a patterned liquid crystal polymer film, e.g., according to the following method. A polymerizable nematic liquid crystal mixture containing a photoisomerizable polymerizable mesogenic compound is coated as a thin film onto a substrate and aligned into uniform orientation. Selected regions of the coated film are then subjected to photoirradiation, e.g., through a photomask. This causes isomerization of the photoisomerizable compound, leading to a change of the alignment in the irradiated regions, e.g., from nematic orientation to a distorted orientation or to an isotropic unoriented state, and thus to a pattern in the film. The pattern is then frozen in by in-situ polymerization of the coated film, e.g., by thermal or photopolymerization.

The patterned films can be used as optical element like colour filters or polarization beam splitters, as information storage device, anisotropic membranes for the permeation of, e.g., gases, or in nonlinear optics.

Gangadhara and Kishore in Macromolecules, 1995, 28, 806–815, the entire disclosure of which is incorporated into this application by way of reference, have reported that polymerizable mesogenic compounds comprising a bis (benzylidene)-cyclohexanone unit undergo EZ photoisomerisation and change from the EE conformation to the isomeric EZ, or ZZ forms as shown below.

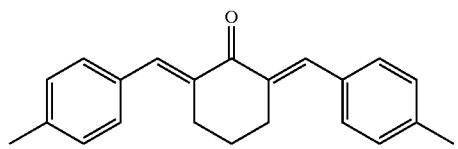

EE

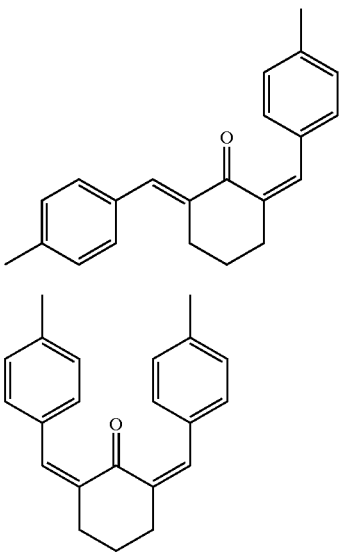

EZ

ZZ

The EZ photoisomerisation is reported to disrupt the parallel stacking of the mesogens, resulting in the transition from the liquid crystal phase to the isotropic phase.

However, the article of Gangadhara and Kishore only discloses compounds having mono-polymerizable groups and mono-mesogenic groups attached the central cyclohexanone core. Furthermore, the compounds disclosed in this article only have narrow liquid crystal phase ranges with low clearing points, or do not show a liquid crystal phase at all.

Therefore, there is a demand for photoisomerizable compounds which are easy to synthesize in a large range of derivatives, show broad liquid crystalline phases with high clearing points and, when added to a liquid crystalline host mixture, do not affect the properties of the host mixture.

The invention has the aim of providing novel compounds having the above properties, but not having the disadvantages of the compounds of discussed above. Another aim of the invention is to extend the pool of photoisomerizable compounds available in the art.

It has been found that the above aims can be achieved by providing cycloalkanone derivatives as described herein.

Definition of Terms

The terms 'liquid crystalline or mesogenic material' or 'liquid crystalline or mesogenic compound' denotes materials or compounds comprising one or more rod-shaped, lath-shaped or disk-shaped mesogenic groups, i.e., groups with the ability to induce liquid crystal phase behavior. Rod-shaped and lath-shaped mesogenic groups are especially preferred. The compounds or materials comprising mesogenic groups do not necessarily have to exhibit a liquid crystal phase themselves. It is also possible that they show liquid crystal phase behavior only in mixtures with other compounds, or when the mesogenic compounds or materials, or the mixtures thereof, are polymerized.

The term 'reactive mesogen' means a polymerizable mesogenic compound.

For the sake of simplicity, the term 'liquid crystal material' is used hereinafter for both liquid crystal materials and mesogenic materials.

The term 'film' includes self-supporting, i.e., free-standing, films that show more or less pronounced mechanical stability and flexibility, as well as coatings or layers on a supporting substrate or between two substrates.

The term 'photoisomerizable group' means a group that shows isomerization, for example, cis-trans or E-Z isomerization, imparting a change in shape upon photoirradiation with a suitable wavelength, preferably in the range from 250 to 400 nm, very preferably from 300 to 400 nm.

SUMMARY OF THE INVENTION

One object of the invention is providing cycloalkanone derivatives of formula I

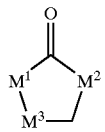

I wherein $M^1$ and $M^2$ are independently of each other C=CH-$A^1$-($Z^1$-$A^2$)$_m$—R, wherein the first carbon is in the ring, one of $M^1$ and $M^2$ may also denote O, S or $CH_2$, $M^3$ is $(CH_2)_k$ wherein one $CH_2$ group may also be replaced by $NR^0$, O or S, k is 1, 2, 3 or 4, $A^1$ and $A^2$ are independently of each other 1,4-phenylene in which, in addition, one or more CH groups may be replaced by N, 1,4-cyclohexylene in which, in addition, one or two non-adjacent $CH_2$ groups may be replaced by O and/or S, 1,3-dioxolane-4,5-diyl, 1,4-cyclohexenylene, piperidine-1,4-diyl, 1,4-bicyclo-(2,2,2)-octylene, naphthalene-2,6-diyl, decahydro-naphthalene-2,6-diyl, 1,2,3,4-tetrahydronaphthalene-2,6-diyl or indane-2,5-diyl, it being possible for all these groups to be unsubstituted, mono- or polysubstituted with L, L is halogen, CN, SCN, $NO_2$, $SF_5$ or an alkyl, alkoxy, alkylcarbonyl or alkoxycarbonyl group with 1 to 4 C atoms, wherein one or more H atoms may be substituted with F or Cl, Z is in each case independently —O—, —S—, —CO—, —COO—, —OCO—, —CO—$NR^0$—, —$NR^0$—CO—, —$CH_2CH_2$—, —$CF_2CF_2$—, —$CH_2CF_2$—, —$OCH_2$—, —$CH_2O$—, —$SCH_2$—, —$CH_2S$—, —$CF_2O$—, —$OCF_2$—, —CH=CH—, —CF=CF—, —CH=CF—, —$(CH_2)_4$—, —CH=CH—COO—, —OCO—CH=CH—, —OOC—$CHR^{00}$—OOC—,—COO—$CHR^{00}$—COO—, —C≡C— or a single bond, m is 0, 1 or 2, $R^0$ is H or alkyl with 1 to 4 C atoms, $R^{00}$ is straight chain or branched alkyl or alkoxy with 1 to 8 C atoms or phenyl that is optionally mono- or polysubstituted by L, R is H, halogen, $NO_2$, CN, SCN, $SF_5$, straight chain, branched or cyclic alkyl with 1 to 25 C atoms wherein one or more $CH_2$ groups can also be replaced by —O—, —S—, —CO—, —$NR^0$—, —CH=CH—, —C≡C— in such a manner that O and/or S atoms are not linked directly to one another, and wherein one or more H-atoms can also be replaced by F, Cl or phenyl that is optionally mono- or polysubstituted by L, or P—(Sp-X)$_n$—, P is a polymerizable group, Sp is a spacer group with 1 to 20 C atoms, X has one of the meanings of Z, and n is 0 or 1.

Another object of the invention is a liquid crystalline mixture containing at least one compound of formula I.

Another object of the present invention is a polymerizable liquid crystalline mixture comprising at least two compounds, at least one of which is a compound of formula I and at least one of which is a polymerizable compound.

Another object of the invention is a chiral linear or crosslinked anisotropic polymer obtainable by polymerizing a polymerizable liquid crystalline mixture comprising one or more compounds of formula I.

Another object of the invention is the use of a compound of formula I, mixture or polymer as described above in optical and electrooptical devices like liquid crystal displays or projection systems, such as STN, TN, AMD-TN, temperature compensation, ferroelectric, guest-host, phase change or surface stabilized or polymer stabilized cholesteric texture (SSCT, PSCT) displays, in optical elements, like reflective polarizers, retardation films, compensators, color filters, polarization beam splitters or holographic elements, especially in reflective films with patterned optical properties, in adhesives, synthetic resins with anisotropic mechanical properties like, for example anisotropic membranes for the permeation of gases or fluids, cosmetic and pharmaceutical compositions like, for example, UV absorbers, UV filters or sunscreens, diagnostics, liquid crystal pigments, for decorative and security applications, especially in security markings that are applied to items or documents of value for easy identification or prevention of falsification, in nonlinear optics, optical recording or information storage, or as dopants.

Another object of the invention is an anisotropic polymer film comprising a compound of formula I.

Another object of the invention is an anisotropic polymer film with patterned optical properties comprising a compound of formula I.

Upon further study of the specification and appended claims, further objects and advantages of this invention will become apparent to those skilled in the art.

The inventive compounds are mesogenic or liquid crystalline, i.e., they can induce or enhance mesophase behavior for example in a mixture with other compounds or exhibit one or more mesophases themselves. It is also possible that the inventive compounds show mesophase behavior only in mixtures with other compounds, or, in case of polymerizable compounds, when being (co)polymerized. Mesogenic inventive compounds are especially preferred.

The inventive compounds have several advantages they can easily be synthesized, also on large scale of several hundred grams, with a broad range of derivatives using standard methods that are known from the literature, the starting materials can be obtained commercially or synthesized cheaply using methods known from the literature they exhibit a good solubility in liquid crystalline mixtures, they exhibit broad liquid crystalline phases.

Photolysis of the compounds of formula I with, e.g., UV light of 360 nm has the effect of isomerizing the double bond of the cycloalkanone group from E to Z, thus completely changing the shape of the molecule and hence the physical molecular properties. The inventive compounds of formula I can be mixed with other polymerizable mesogenic compounds to give a liquid crystalline mixture. If such a liquid crystalline mixture, for example, a nematic mixture is aligned on a surface and then photolysed with, e.g., UV light of 360 nm, the light changes the shape of the isomerizable dopant—this in turn disrupts the parallel alignment of the mixture, and this has an overall effect of reducing the birefringence of the mixture.

If irradiation is carried out through a mask towards a liquid crystalline mixture doped with the photoisomerizable compound, and the resulting film is viewed between crossed polarizers, the change of birefringence shows a lower retardation in areas of higher UV transmission.

The compounds of formula I are thus useful, e.g., for forming optical films with novel architectures.

Preferred are compounds of formula I wherein $M^3$ is O, S, NH, N(CH$_3$), CH$_2$, (CH$_2$)$_2$, CH$_2$O, OCH$_2$, CH$_2$S or SCH$_2$.

In the case that both $M^1$ and $M^2$ in formula I denote C=CH-A$^1$-(Z$^1$-A$^2$)$_m$—R, the C=CH-double bond adjacent to the cyclolkanone ring in both groups has preferably the same stereoconformation. Very preferably the compound has EE conformation. The two groups C=CH-A$^1$-(Z$^1$-A$^2$)$_m$—R on both sides of the cycloalkanone ring may be identical or different, they may differ, e.g., in the meaning of m, R, Z, A$^1$ and/or A$^2$.

The compounds of formula I preferably comprise one or two, very preferably two polymerizable groups.

In formula I k is preferably 1 or 2, m is preferably 1 or 2, in particular 1, and n is preferably 1.

Particularly preferred are compounds of formula I wherein the group A$^1$-(Z$^1$-A$^2$)$_m$ is selected from the group of formulae listed below. For reasons of simplicity, Phe in these formulae is 1,4-phenylene that may also be substituted with 1 to 4 groups L as defined in formula II, Cyc is 1,4-cyclohexylene and Z has one of the meanings of formula II. The list is comprising the following subformulae as well as their mirror images

|  |  |
|---|---|
| —Phe—Z—Phe— | II-1 |
| —Phe—Z—Cyc— | II-2 |
| —Cyc—Z—Cyc— | II-3 |
| —Phe—Z—Phe—Z—Phe— | II-4 |
| —Phe—Z—Phe—Z—Cyc— | II-5 |
| —Phe—Z—Cyc—Z—Phe— | II-6 |
| —Cyc—Z—Phe—Z—Cyc— | II-7 |
| —Phe—Z—Cyc—Z—Cyc— | II-8 |
| —Cyc—Z—Cyc—Z—Cyc— | II-9 |

Particularly preferred are the subformulae II-1, II-2, II-4, II-5 and II-6.

Z is preferably —COO—, —OCO—, —CH$_2$CH$_2$— or a single bond.

A particularly preferred embodiment relates to compounds wherein at least one group Z is a chiral group OOC—CHR$^{oo}$—OOC or COO—CHR$^{oo}$—COO. R$^{oo}$ in these groups is preferably phenyl or straight-chain or branched alkyl with 2 to 5 C atoms, very preferably phenyl or 2-methylpropyl.

Very preferably the group A$^1$-Z$^1$-(A$^2$—Z$^2$)$_m$ is selected from the following formulae and their mirror images

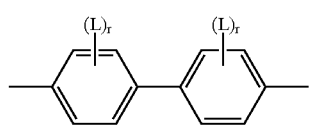

IIa

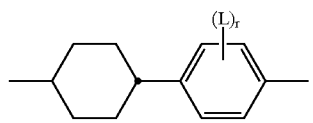

IIb

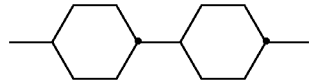

IIc

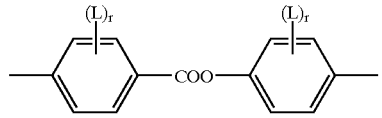

IId

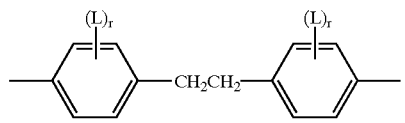

IIe

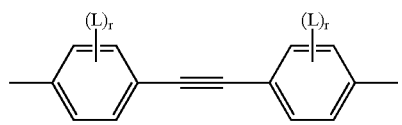

IIf

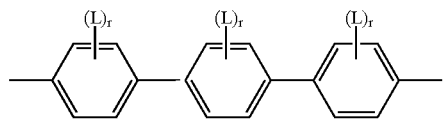

IIg

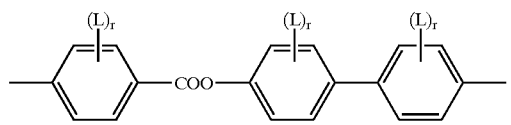

IIh

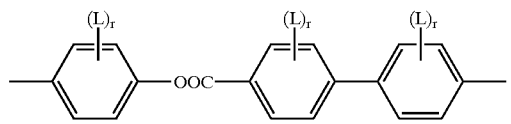

IIi

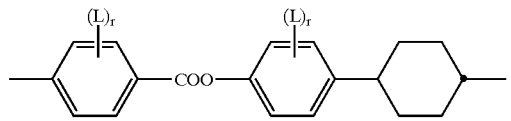

IIk

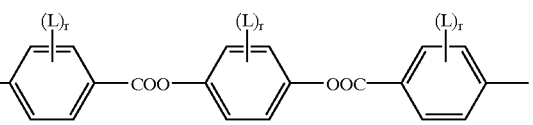

IIm

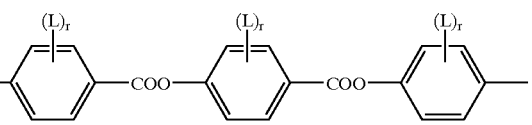

IIn

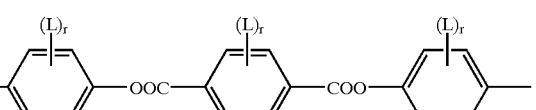

IIo

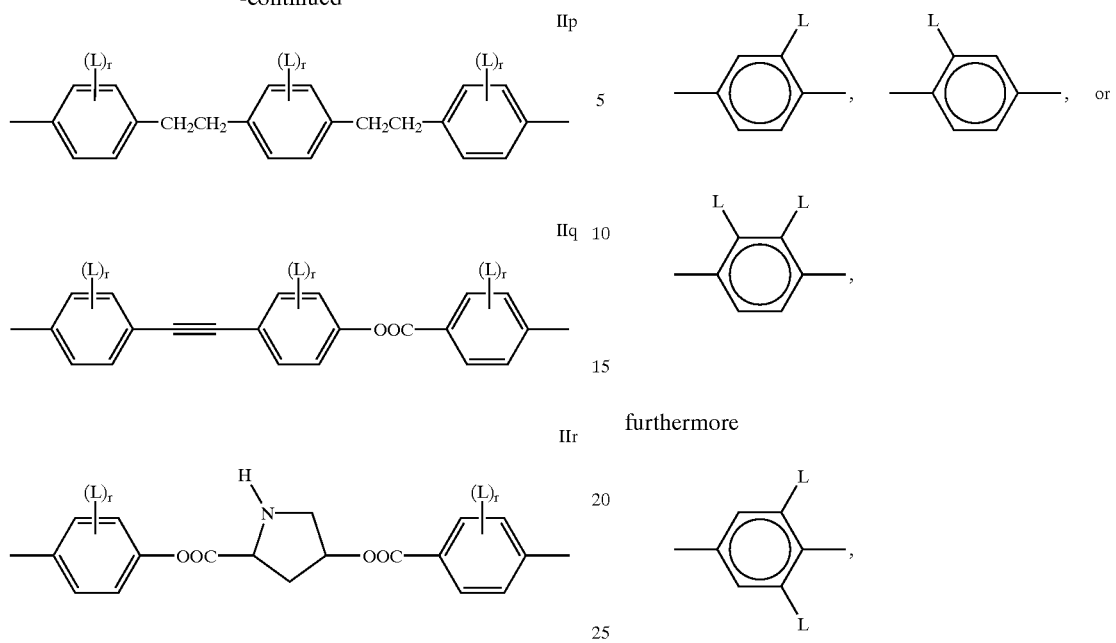

wherein L and r have the above meanings, and r is preferably 0, 1 or 2.

The group

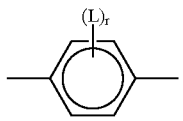

in these preferred formulae is very preferably denoting with L having each independently one of the meanings given above.

Particularly preferred are the subformulae IId, IIg, IIh, IIi, IIm, IIn and IIo, in particular the subformulae IId.

L is preferably F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$ or $OC_2F_5$, in particular F, Cl, CN, $CH_3$, $C_2H_5$, $OCH_3$, $COCH_3$, $CF_3$ or $OCF_3$, most preferably F, Cl, $CH_3$, $OCH_3$ or $OCF_3$.

Particularly preferred compounds of formula I are those of the following subformulae

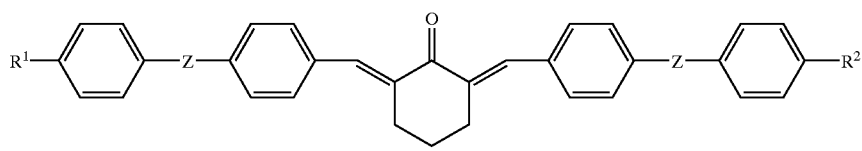

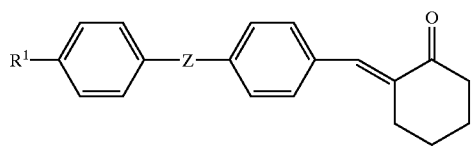

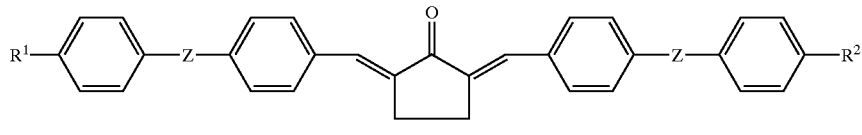

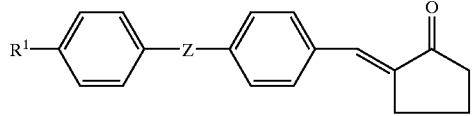

wherein

Z is as defined in formula I, $R^1$ and $R^2$ are independently of each other P—(Sp-X)$_n$— or $R^3$, and $R^3$ is H, halogen, NO$_2$, CN, SCN, SF$_5$, straight chain, branched or cyclic alkyl with 1 to 25 C atoms wherein one or more CH$_2$ groups can also be replaced by —O—, —S—, —CO—, —NR$^0$—, —CH=CH—, —C≡C— in such a manner that O and/or S atoms are not linked directly to one another, and wherein one or more H-atoms can also be replaced by F or Cl.

Particularly preferred are compounds of formula Ia to Id wherein both $R^1$ and $R^2$ denote P—(Sp-X)$_n$—. Further preferred are compounds of formula Ia and Ic wherein both $R^1$ and $R^2$ denote $R^3$. Further preferred are compounds of formula Ia and Ic wherein one of $R^1$ and $R^2$ is P—(Sp-X)$_n$— and the other is $R^3$.

$R^3$ and R are preferably different from H.

If R or $R^3$ is an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Especially preferred is straight chain alkyl or alkoxy with 1 to 8 C atoms.

Oxaalkyl, i.e. where one CH$_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl 2-, 3-, 4-, 5-, 6-, 7- or 8-oxanonyl or 2-, 3-, 4-, 5-, 6-, 7-, 8- or 9-oxadecyl, for example.

R and $R^3$ can be a polar or an unpolar group.

In case of a polar group, it is preferably selected from CN, NO$_2$, halogen, OCH$_3$, SCN, COR$^8$, COOR$^8$ or a mono- oligo- or polyfluorinated alkyl or alkoxy group with 1 to 4 C atoms. $R^8$ is optionally fluorinated alkyl with 1 to 4, preferably 1 to 3 C atoms. Especially preferably polar groups are selected of F, Cl, CN, NO$_2$, OCH$_3$, COCH$_3$, COC$_2$H$_5$, COOCH$_3$, COOC$_2$H$_5$, CF$_3$, C$_2$F$_5$, OCF$_3$, OCHF$_2$, and OC$_2$F$_5$, in particular of F, Cl, CN, OCH$_3$ and OCF$_3$.

In case of an unpolar group, it is preferably alkyl with 1 to 15 C atoms or alkoxy with 2 to 15 C atoms.

R and $R^3$ can be an achiral or a chiral group. In case of a chiral group, it is preferably selected according to formula IV:

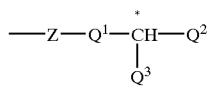

IV wherein $Z^3$ is —O—, —S—, —CO—, —COO—, —OCO—, —OCOO— or a single bond, $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted with halogen or CN, it being also possible for one or more non-adjacent CH$_2$ groups to be replaced, in each case independently from one another, by —C≡C—, —O—, —S—, —NR$^0$—, —CO—, —COO—, —OCO—, —OCO—O—, —S—CO— or —CO—S— in such a manner that oxygen atoms are not linked directly to one another, $Q^3$ is halogen, a cyano group, an alkyl or alkoxy group with 1 to 4 C atoms different from $Q^2$, or a phenyl group that may also be mono- or polysubstituted with L as defined in formula I.

In case $Q^1$ in formula IV is an alkylene-oxy group, the O atom is preferably adjacent to the chiral C atom.

Preferred chiral groups are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl, 1,1,1-trifluoro-2-alkoxy, 2-phenylalkyl, 2-phenylalkoxy, 2-phenylcarbonyl, 2-phenylcarbonyloxy and 2-phenyloxycarbonyl.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy, 2-phenylbutyl, 2-phenylbutyloxy, 2-phenylpropylcarbonyl, 2-phenylpropylcarbonyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy, for example.

In addition, compounds of formula I containing an achiral branched group R or $R^3$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

Another preferred embodiment of the present invention relates to compounds of formula I wherein R, $R^1$ or $R^2$ is denoting P—(Sp-X)$_n$.

$R^0$ in formula I is preferably H or CH$_3$, in particular H.

The polymerizable group P is preferably selected from CH$_2$=CW$^1$—COO—,

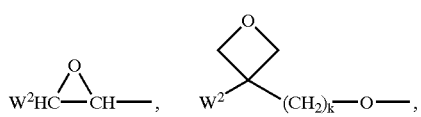

CH$_2$=CW$^2$—O—, CH$_3$—CH=CH—O—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-phe-(O)$_{k2}$—, -phe-CH=CH—, HOOC—, OCN— and W$^4$W$^5$W$^6$Si—, with W$^1$ being H, Cl, CN, phenyl or alkyl with 1 to 5 C-atoms, in particular H, Cl or CH$_3$, W$^2$ and W$^3$ being independently of each other H or alkyl with 1 to 5 C-atoms, in particular methyl, ethyl or n-propyl, W$^4$, W$^5$ and W$^6$ being independently of each other Cl, oxaalkyl or oxacarbonylalkyl with 1 to 5 C-atoms, Phe being 1,4-phenylene and $k_1$ and $k_2$ being independently of each other 0 or 1.

P is particularly preferably an acrylate, methacrylate, vinyl, vinyloxy, epoxy, styrene or propenyl ether group, in particular an acrylate, methacrylate, vinyl or epoxy group.

As spacer group Sp in formula I all groups can be used that are known for this purpose to the skilled in the art. Sp is preferably a straight chain or branched alkylene group having 1 to 20 C atoms, in particular 1 to 12 C atoms, in which, in addition, one or more non-adjacent $CH_2$ groups may be replaced by —O—, —S—, —$NR^o$—, —CO—, —O—CO—, —S—CO—, —O—COO—, —CO—S—, —CO—O—, —CH(halogen)-, —CH(CN)—, —CH(OH)—, —$(CF_2)_x$—, —$(CD_2)_x$—, —CH=CH—, —CF=CF—, —CH=CF— or —C≡C—, with x being an integer from 1 to 12, and in which one or more H atoms may be replaced by halogen, CN or OH.

Typical spacer groups are for example —$(CH_2)_y$—, —$(CH_2CH_2O)_z$—$CH_2CH_2$—, —$CH_2CH_2$—S—$CH_2CH_2$— or —$CH_2CH_2$—NH—$CH_2CH_2$—, with y being an integer from 2 to 12 and p being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Especially preferred are inventive compounds of formula I wherein Sp is denoting alkylene or alkylene-oxy with 2 to 8 C atoms. Straight-chain groups are especially preferred.

In another preferred embodiment of the invention the compounds of formula I comprise at least one spacer group Sp that is a chiral group of formula V:

wherein
$Q^1$ and $Q^3$ have the meanings given in formula IV, and
$Q^4$ is an alkylene or alkylene-oxy group with 1 to 10 C atoms or a single bond, being different from $Q^1$.

In case $Q^1$ in formula V is an alkylene-oxy group, the O atom is preferably adjacent to the chiral C atom.

Throughout this text, halogen is preferably F or Cl.

The inventive compounds can be synthesized according to or in analogy to methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here. Further methods for preparing the inventive compounds can be taken from the examples.

In particular, the inventive compounds can be prepared according to or in analogy to the following reaction schemes.

Scheme 1

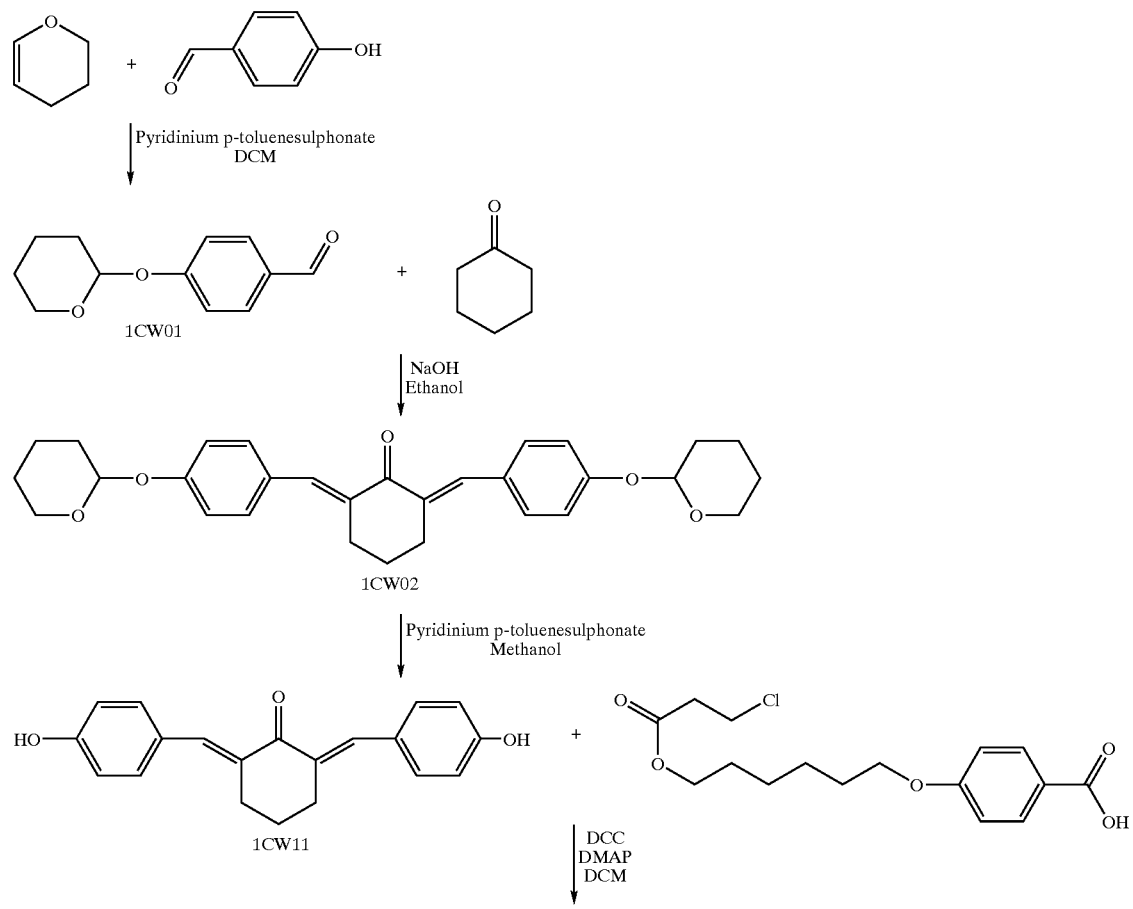

-continued
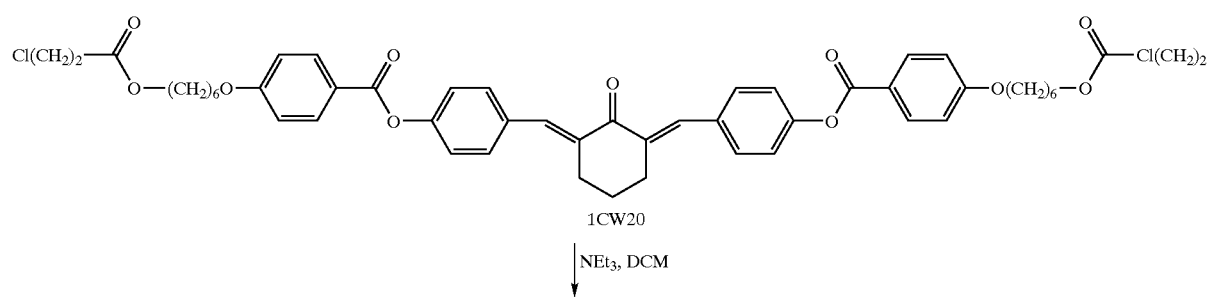
1CW20
NEt₃, DCM
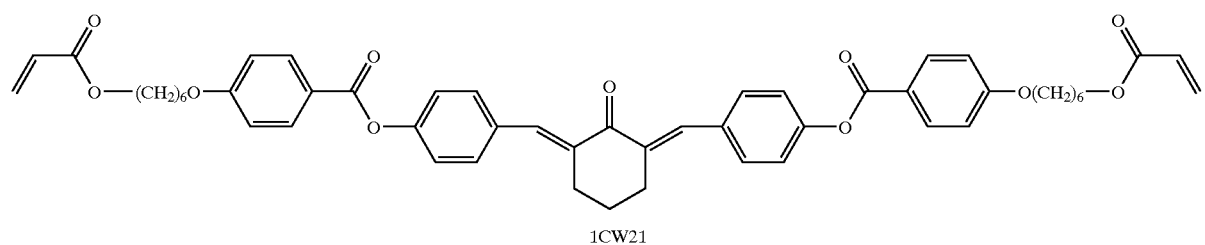
1CW21
Scheme 2
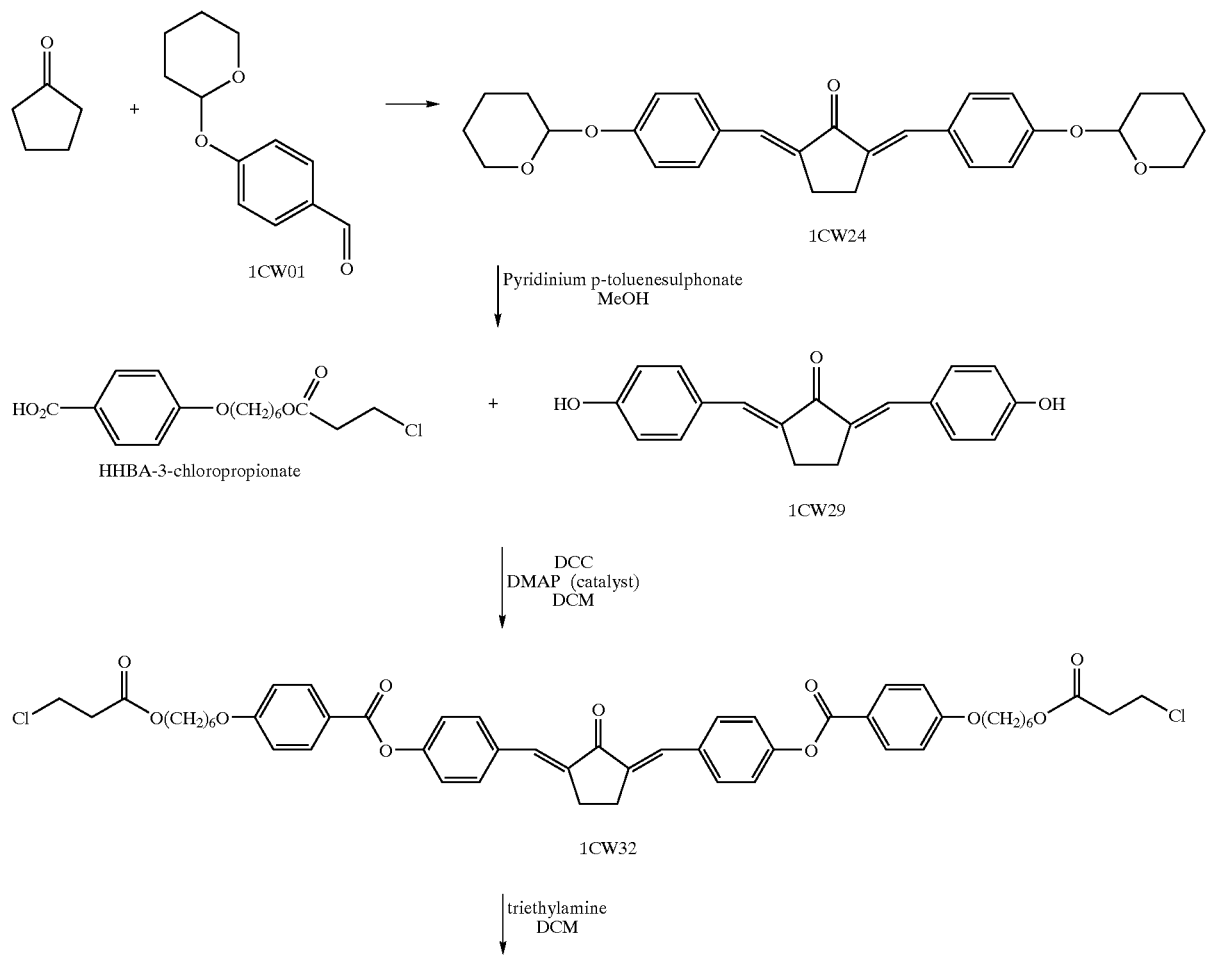

-continued

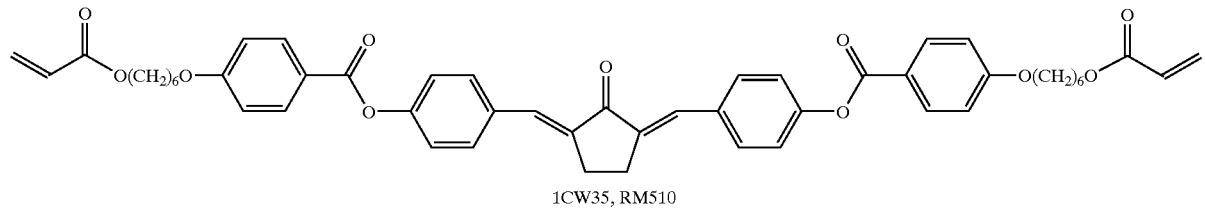

1CW35, RM510

The inventive compounds can be used in a liquid crystal mixture for liquid crystal displays. Thus, another object of the invention is a liquid crystalline mixture comprising at least one compound of formula I.

Many of the inventive compounds are characterized by a good solubility in liquid crystalline host mixtures, and can be added as dopants to liquid crystalline hosts in high amounts without significantly affecting the phase behaviour and electrooptical properties of the mixture. Undesired spontaneous crystallization at low temperatures is thereby reduced and the operating temperature range of the mixture can be broadened.

A liquid crystalline mixture according to the invention comprises preferably 0.1 to 30%, in particular 1 to 25% and very particularly preferably 2 to 15% by weight of compounds of formula I.

A liquid crystalline mixture according to the invention preferably comprises 1 to 3 chiral compounds of formula I.

In a preferred embodiment of the invention the liquid crystalline mixture is consisting of 2 to 25, preferably 3 to 15 compounds, at least one of which is a compound of formula I. The other compounds are preferably low molecular weight liquid crystalline compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally-mono- or difluorinated.

The liquid crystalline mixture of this preferred embodiment is based on the achiral compounds of this type.

The most important compounds that are posssible as components of these liquid crystalline mixtures can be characterized by the following formula

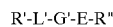

wherein L' and E, which may be identical or different, are in each case, independently from one another, a bivalent radical from the group formed by Phe-, -Cyc-, -Phe-Phe-, -Phe-Cyc-, -Cyc-Cyc-, -Pyr-, -Dio-, -B-Phe-and -B-Cyc-and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH═CH—, —N(O)N—, —CH═CY—, —CH═N(O)—, —C≡C—, —CH$_2$—CH$_2$—, —CO—O—, —CH$_2$—O—, —CO—S—, —CH$_2$—S—, —CH═N—, —COO-phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

A preferred use of the inventive compounds is the preparation of polymerizable liquid crystalline mixtures, anisotropic polymer gels and anisotropic polymer films, in particular oriented polymer films that exhibit a pattern of different regions with different orientation as describe above.

Patterned polymer films can be used for example as optical elements like color filters or polarization beam splitters, alignment layers, security markings or anisotropic membranes for the permeation of gases or fluids. Furthermore, the inventive polymers and polymer gels can eb used in optical information storage devices or nonlinear optics.

For the preparation of anisotropic polymer gels or oriented polymer films, the liquid crystalline mixture should comprise at least one polymerizable compound, preferably a polymerizable mesogenic compound.

Thus, another object of the invention is polymerizable liquid crystalline mixtures comprising at least two compounds, at least one of which is a compound of formula I and at least one of which is a polymerizable compound. The polymerizable compound can be at least one compound of formula I or an additional compound.

Examples of suitable polymerizable mesogenic compounds that can be used as co-components in the polymerizable mixture are disclosed for example in WO 93/22397; EP 0,261,712; DE 195,04,224; WO 95/22586 and WO 97/00600. The compounds disclosed in these documents, however, are to be regarded merely as examples that shall not limit the scope of this invention. Preferably the polymerizable mixture comprises at least one polymerizable mesogenic compound having one polymerizable functional group and at least one polymerizable mesogenic compound having two or more polymerizable functional groups.

Examples of especially useful monoreactive chiral and achiral polymerizable mesogenic compounds are shown in the following list of compounds, which should, however, be taken only as illustrative and is in no way intended to restrict, but instead to explain the present invention:

wherein, P has one of the meanings given above, x is an integer from 1 to 12, A is 1,4-phenylene or 1,4-cyclohexylene, v is 0 or 1, $Y^0$ is a polar group, $R^7$ is an unpolar alkyl or alkoxy group, Ter is a terpenoid radical like e.g. menthyl, Chol is a cholesteryl group, and $L^1$ and $L^2$ are each independently H, F, Cl, CN, OH, $NO_2$ or an optionally halogenated alkyl, alkoxy or carbonyl group with 1 to 7 C atoms.

The polar group $Y^0$ is preferably CN, $NO_2$, halogen, $OCH_3$, OCN, SCN, $COR^8$, $COOR^8$ or a mono- oligo- or polyfluorinated alkyl or alkoxy group with 1 to 4 C atoms. $R^8$ is optionally fluorinated alkyl with 1 to 4, preferably 1 to 3 C atoms. Especially preferably the polar group $Y^0$ is selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular F, Cl, CN, $OCH_3$ and $OCF_3$.

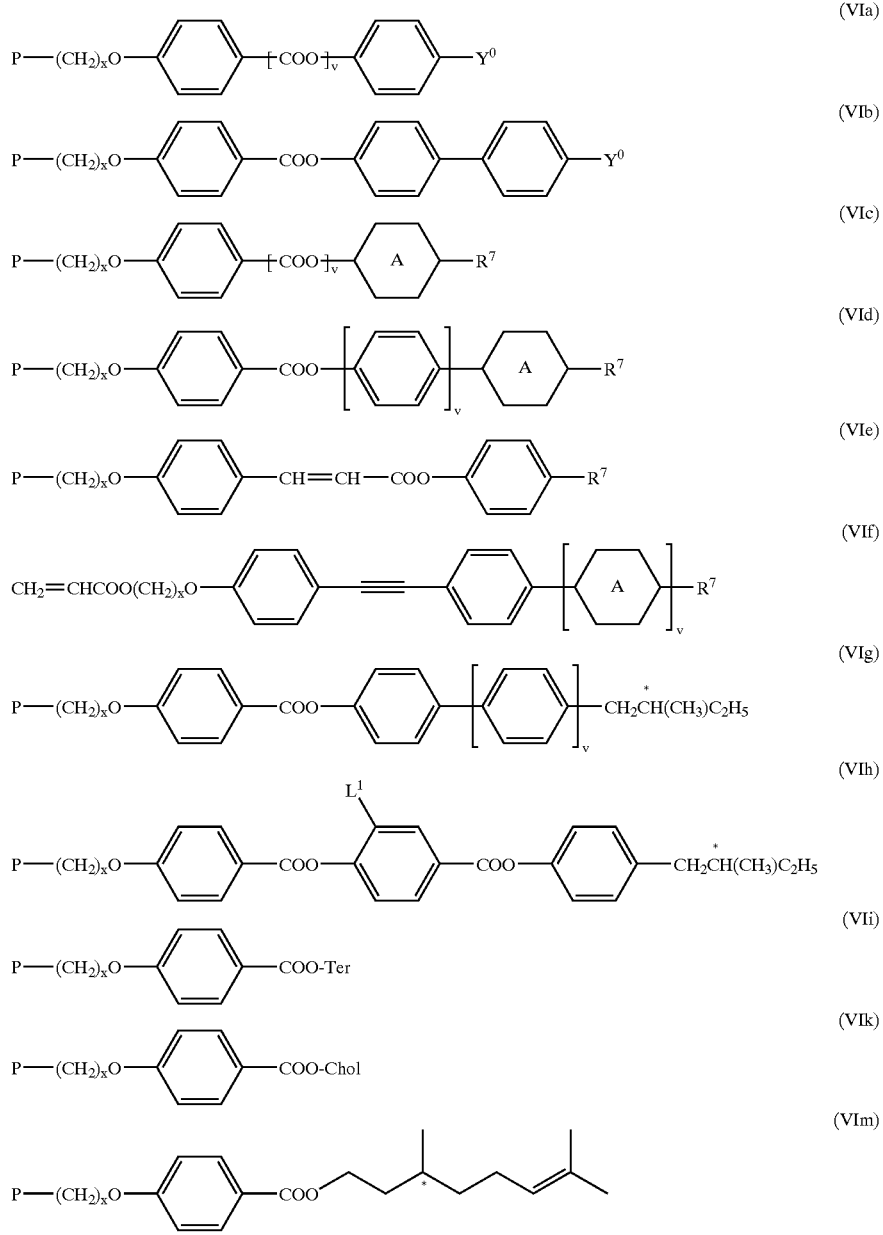

(VIa)

(VIb)

(VIc)

(VId)

(VIe)

(VIf)

(VIg)

(VIh)

(VIi)

(VIk)

(VIm)

The unpolar group $R^7$ is preferably an alkyl group with 1 or more, preferably 1 to 15 C atoms or an alkoxy group with 2 or more, preferably 2 to 15 C atoms.

Examples of useful direactive chiral and achiral polymerizable mesogenic compounds are shown in the following list of compounds, which should, however, be taken only as illustrative and is in no way intended to restrict, but instead to explain the present invention Another object of the invention is an anisotropic polymer film with an oriented chiral liquid crystalline phase obtainable by (co)polymerizing a liquid crystalline mixture comprising at least one compound of formula I and at least one polymerizable mesogenic compound preferably selected of formula VIa-VIm and VIIa-VIIe and/or at least one polymerizable compound of formula I.

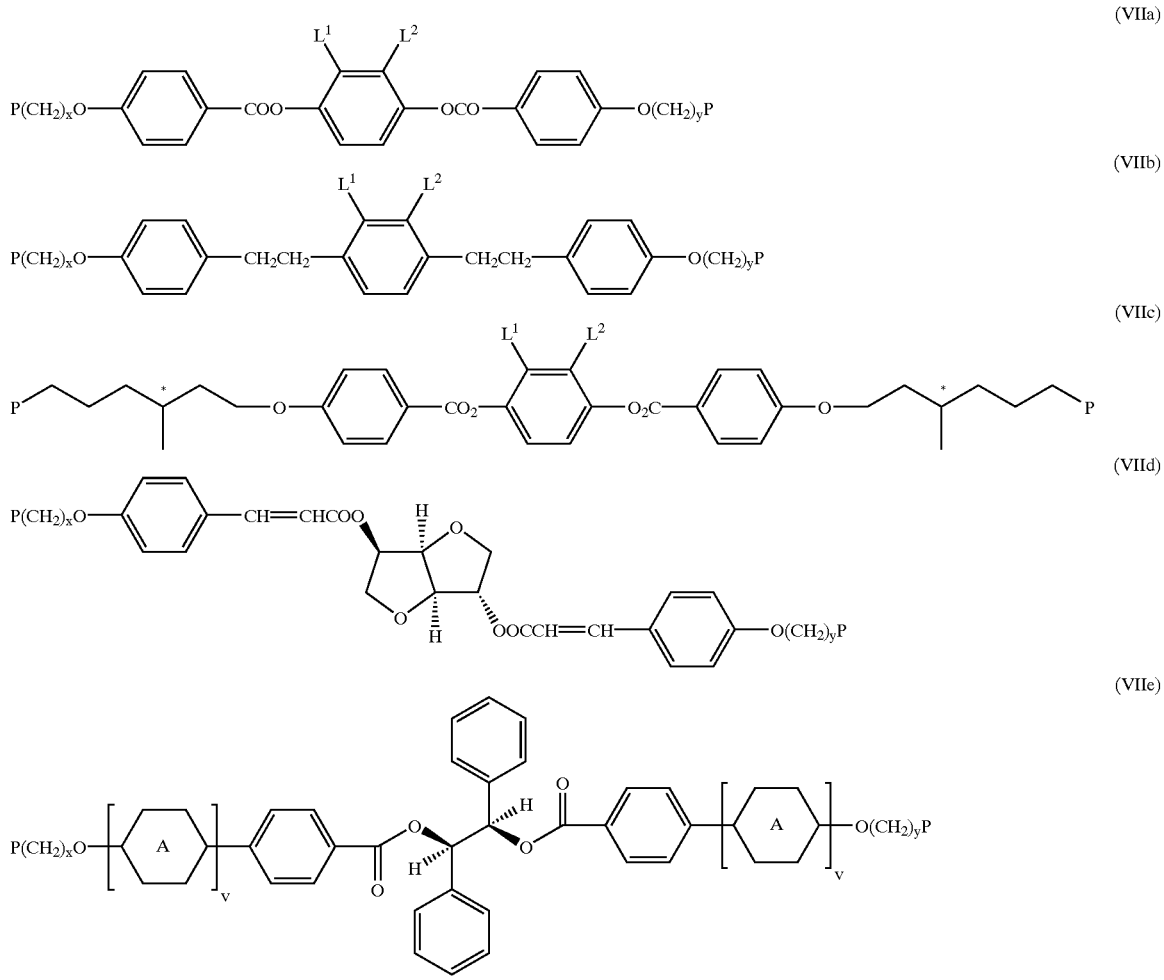

wherein P, x, A, $L^1$ and $L^2$ have one of the meanings given above and y is an integer from 1 to 12 the same as or different from x.

The mono- and difunctional polymerizable mesogenic compounds of above formulae VI and VII can be prepared by methods which are known per se and which are described in the documents cited above and, for example, in standard works of organic chemistry such as, for example, Houben-Weyl, Methoden der organischen Chemie, Thieme-Verlag, Stuttgart.

In a preferred embodiment of the invention the polymerizable liquid crystalline mixtures comprise at least one inventive compound of formula I, at least one monofunctional compound of formulae VIa-VIm and at least one bifunctional polymerizable compound of formulae VIIa-VIIe.

In another preferred embodiment the polymerizable liquid crystalline mixtures comprise at least one inventive compound of formula I and at least two monofunctional compounds of formulae VIa-VIm.

The preparation of an anisotropic polymer film from a polymerizable mixture is generally described for example in D. J. Broer, et al., Angew. Makromol. Chem. 183, (1990), 45–66. The cholesteric polymerizable mixture is coated onto a substrate, aligned into uniform planar orientation, and polymerized in situ by exposure to heat or actinic radiation, thereby fixing the uniform alignment. Alignment and curing are carried out in the liquid crystal phase of the polymerizable mixture.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

For example, when photopolymerizing by means of UV light, a photoinitiator can be used that decomposes under UV irradiation to produce free radicals or ions that start the polymerization reaction. It is also possible to use a cationic photoinitiator, when curing polymerizable mesogens with for example vinyl and epoxide reactive groups, that photocures with cations instead of free radicals. As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used. Preferably the polymerizable liquid crystalline mixtures comprising polymerizable compounds of formula I and/or polymerizable mesogenic compounds of formulae VI and VII additionally comprise 0.01 to 10%, in particular 0.05 to 8%, very preferably 0.1 to 5% by weight of a photoinitiator, especially preferably a UV-photoinitiator.

Preferably polymerization is carried out under an atmosphere of inert gas, preferably under a nitrogen atmosphere.

As a substrate for example a glass or quartz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization. Isotropic or birefringent substrates can be used. In case the substrate is not removed from the polymerized film after polymerization, preferably isotropic substrates are used. Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

The polymerizable mixture is preferably coated as a thin layer on a substrate or between substrate, and aligned in its liquid crystal phase, e.g. the nematic or smectic phase, to give a planar orientation, i.e. wherein the optical axis of the liquid crystal material is parallel to the plane of the layer. Planar orientation can be achieved for example by shearing the mixture, e.g. by means of a doctor blade. It is also possible to apply an alignment layer, for example a layer of rubbed polyimide or sputtered $SiO_x$, on top of at least one of the substrates. Alternatively, a second substrate is put on top of the coated material. In this case, the shearing caused by putting together the two substrates is sufficient to give good alignment. It is also possible to apply an electric or magnetic field to the coated mixture.

In some cases it is of advantage to apply a second substrate not only to aid alignment of the polymerizable mixture but also to exclude oxygen that may inhibit the polymerization. Alternatively curing can be carried out under an atmosphere of inert gas. However, curing in air is also possible using suitable photoinitiators and high lamp power. When using a cationic photoinitiator oxygen exclusion most often is not needed, but water should be excluded.

An inventive polymerizable liquid crystalline mixture for the preparation of anisotropic polymer films comprises preferably 0.1 to 35%, in particular 0.5 to 15% and very particularly preferably 0.5 to 5% by weight of one or more polymerizable chiral compounds of formula I. Polymerizable liquid crystalline mixtures are preferred that comprise 1 to 3 chiral compounds of formula I.

The inventive polymerizable liquid crystalline mixtures can additionally comprise one or more other suitable components such as, for example, catalysts, sensitizers, stabilizers, inhibitors, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Preferably the inventive polymerizable mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add a non mesogenic compound with two or more polymerizable functional groups, preferably in an amount of up to 20% by weight, to the polymerizable mixture alternatively or additionally to multifunctional mesogenic polymerizable compounds. Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystalline mixtures can be polymerized in situ as described above, however, in this case alignment of the polymerizable mixture is not always necessary.

Due to the presence of a photoisomerizable group in the compounds of formula I, the orientation of the inventive compounds and liquid crystalline mixtures can be changed by photoirradiation. Photoirradiation can be achieved for example with irradiation by UV light or other high energy sources such as lasers.

The compounds of formula I and the liquid crystalline mixtures and polymers comprising them are useful in optical and electrooptical devices like liquid crystal displays or projection systems, patterned films and optical elements like polarizers, retardation films, compensators, color filters, holographic elements or polarization beam splitters, for photoswitching, in anisotropic membranes for the permeation of gases or fluids, adhesives, synthetic resins with anisotropic mechanical properties, cosmetic or pharmaceutical compositions, UV absorbers and sunscreens, diagnostics or liquid crystal pigments, for decorative and security applications, in nonlinear optics, optical information storage or as dopants.

The compounds of formula I and liquid crystalline mixtures, liquid crystal polymers or liquid crystal pigments comprising them are also suitable for use in cosmetic and pharmaceutical compositions, for example as UV absorbers or sunscreens for the protection of human skin or hair, in particular protection against UV-A and UV-B-radiation, as described for example in JP 04-134043.

A liquid crystalline mixture, liquid crystal polymer or liquid crystal pigment comprising a compound of formula I and reflecting UV light, in particular of a wavelength of 200 to 400 nm, is another object of the invention. Another object is a cosmetic composition, in particular a cosmetic or pharmaceutical composition for protection of human skin or hair, comprising as UV-filter a compound of formula I or a liquid crystalline mixture, liquid crystal polymer or liquid crystal pigment comprising a compound of formula I and reflecting UV light, in particular in a wavelength range of 200–440 nm, especially 280–400 nm, 200–230 nm (UV-C) and 280–330 nm (UV-B).

Furthermore, the compounds of formula I are particularly suitable for the preparation of patterned films, for example by the following method:

A thin layer of a polymerizable nematic mixture comprising an inventive photoisomerizable compound of formula I is coated as a thin film onto a substrate and aligned into planar orientation as described above. If the coated film is exposed to photoradiation of a suitable wavelength, the compound of formula I shows EZ isomerization if the wavelength of radiation is selected accordingly, e.g. between 300 and 400 nm. This causes a disruption of the planar nematic orientation in the exposed parts of the film, and can even lead to a radiation-induced nematic-isotropic phase transition in the exposed region. Thereby the birefringence is changing in the exposed parts. The partially or totally unoriented state can be fixed by subsequent in-situ polymerization, e.g. by thermal or photocuring.

If only a part of the film is exposed to photoradiation, e.g. by irradiation through a photomask that is applied on top of the coated film, the nematic orientation can be destroyed and the unoriented state subsequently be fixed by thermal or photocuring of the exposed parts. Afterwards the highly oriented state in the previously unexposed parts of the film is also fixed by thermal or photocuring. The sequence of these steps may also be changed, e.g. first fixing of the oriented parts by photocuring through a photomask, and then photoisomerization and fixing of the remaining parts.

The above described methods can also be used to prepare patterned films with chiral liquid crystalline structure, such as e.g. cholesteric or chiral smectic C liquid crystal films.

For example cholesteric liquid crystal films with planar alignment show selective reflection of visible light that is circularly polarized, caused by interaction of incident light with the helically twisted structure of the cholesteric material. If one or more chiral compounds of formula I are added e.g. to nematic or cholesteric polymerizable liquid crystal mixture, photoisomerization of the chiral compounds of formula I leads to a change of their chirality and thus to a change of the helical pitch of the mixture, which is fixed by polymerization. As the pitch is directly proportional to the reflection wavelength of the cholesteric material, patterned cholesteric films having regions of different reflection wavelength can be obtained by using photomask technique as described above.

Such films are suitable for example as color filters in optical or electrooptical devices like liquid crystal displays or projectors. They can also be used for security markings, e.g. to identify or prevent falsification of credit cards, passports, bank notes or other documents of value, for decorative coatings or the preparation of liquid crystal pigments.

Furthermore, cholesteric reflective films exhibiting a change of the pitch in vertical direction, i.e. perpendicular to the film plane, can be prepared. They can be used as broadband reflective polarizers having a broad bandwidth of the reflected wavelength band.

The preparation of patterned cholesteric films is described for example in WO 00/34808 and in P. van de Witte et al., J. Mater. Chem. 9 (1999), 2087–2094, the entire disclosure of which is incorporated into this application by way of reference.

A broadband reflective cholesteric film can e.g. be prepared as follows: A layer of a cholesteric or nematic mixture with planar orientation comprising a chiral photoisomerizable compound of formula I additionally comprises a dye having an absorption maximum at the wavelength where the isomerizable compound shows photoisomerization. For example, the mixture may comprise an isomerizable compound showing isomerization at a wavelength in the UV range together with a UV dye. If the mixture is exposed to UV radiation as described above, the dye will create a gradient in UV light intensity throughout the thickness of the layer. As a consequence, the isomerization is faster at the top of the layer than at the bottom and a pitch gradient is created, leading to a broadening of the reflected wavelength band. The pitch gradient and reflection bandwidth can be controlled for example by varying the film thickness, irradiation time, radiation dose and/or the concentration of the UV dye and the photoisomerizable compound. If the cholesteric mixture comprises one or more polymerizable components, the structure of the film can be fixed by in-situ polymerization.

It is also possible to prepare cholesteric liquid crystal films wherein the pitch varies in horizontal or vertical direction by using an achiral isomerizable compound of formula I together with a cholesteric liquid crystal mixture. As described above, the achiral isomerizable compound changes its shape e.g. due to EZ isomerization under photoirradiation, causing a change of the order parameter and thus of the pitch in the cholesteric mixture in the irradiated regions. If the mixture contains a polymerizable compound, the region with different pitch can be fixed by subsequent in-situ polymerization. Thereby, patterned cholesteric films having regions of different reflection wavelength can be obtained by using photomask technique as described above. Alternatively, a broadband cholesteric film with the pitch varying in vertical direction can be obtained by using e.g. a UV dye that creates an intensity gradient of the photoradiation in vertical direction as described above.

From the foregoing description, one skilled in the art can easily ascertain the essential characteristics of this invention, and without departing from the spirit and scope thereof, can make various changes and modifications of the invention to adapt it to various usages and conditions.

The entire disclosure[s] of all applications, patents and publications, cited above or below, and of corresponding European Patent application No. 01108721.0, filed Apr. 6, 2001, are hereby incorporated by reference.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight.

The following abbreviations are used to illustrate the liquid crystalline phase behavior of the compounds:

K=crystalline; N=nematic; S=smectic; N*, Ch=chiral nematic or cholesteric; I=isotropic. The numbers between these symbols indicate the phase transition temperatures in degree Celsius. Furthermore, mp. is the melting point, Δn is the birefringence at 589 nm and 20° C. and Δε is the dielectric anisotropy at 20° C. C* in a chemical formula denotes a chiral C atom. DCM is dichloromethane.

"Conventional workup" means: water is added if necessary, the mixure is extracted with methylene chloride, diethyl ether or toluene, the phases are separated, the organic phase is dried and concentrated by evaporation, and the product is purified by crystallization and/or chromatography.

EXAMPLE 1

Compound (1a) was prepared according to reaction scheme 1 and as described below stirred at 35° C. overnight. The mixture was poured into water (400 ml). The resulting precipitate was isolated by vacuum filtration, and washed with water (3×30 ml) to leave the product as a green solid (7.62 g, 85%). $^1$H NMR showed expected signals.
1CW20

1CW11 (4.5 g, 0.015 mol), DCC (7.05 g, 0.035 mol), HHBA-3-chloropropionate (10.22 g, 0.031 mol), DMAP (0.27 g) and DCM (200 ml) were stirred for 16 hrs. A solid precipitate was removed by filtration, then the filtrate was washed with water (2×20 ml) dried and evaporated to dryness leaving a yellow solid (9.28 g, 83%). This was used without further purification in the formation of 1CW21.
Compound (1a) (1CW21)

1CW20 (9.28 g, 0.01 mol), DCM (300 ml) and triethylamine (8.3 ml, 0.060 mol) were stirred at 35° C. for 24 h. The mixture was cooled to room temperature, washed with dilute HCl (2×500 ml), water (3×400 ml), dried over sodium

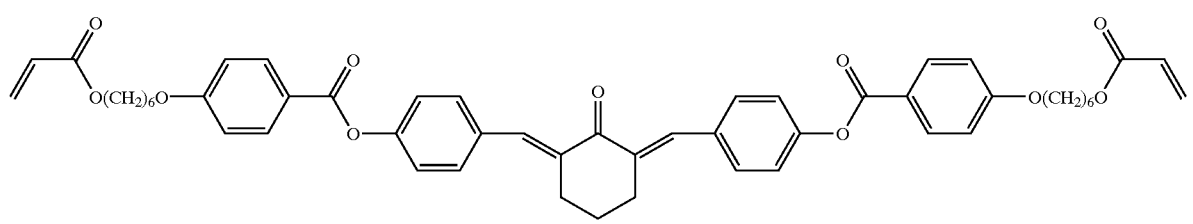

(1a)

4-(Tetrahydro-pyran-2-yloxy)-benzaldehyde (1CW01)

4-Hydroxybenzaldehyde (43.4 g, 0.355 mol), dihydropyran (44.4 ml, 0.495 mol), pyridinium p-toluenesulphonate (11.6 g, 0.046 mol, 0.1 mol equiv.) and dichloromethane (300 ml) were stirred for 16 h at room temperature. The mixture was washed with dilute aqueous sodium hydroxide solution (2×300 ml), water (200 ml), brine (300 ml), and finally with water (250 ml), dried over sodium sulphate and evaporated to dryness to leave a dark brown oil(63 g, 87%). This was used without further purification in the following step 1CW02. $^1$H NMR showed expected signals.
2,6-Bis-[4-(tetrahydro-pyran-2-yloxy)-benzylidene]-cyclohexanone (1CW02)

sulphate and evaporated to dryness. The crude product was purified by flash column chromatography using toluene: ethyl acetate as eluant to give upon evaporation of the appropriate fractions a yellow solid (4.21 g, 49%). $^1$H NMR, $^{13}$C NMR and I.R. showed expected signals, Mass Spec. ES+878.21 (M+Na$^+$), 1732.15 (2M+Na$^+$).

Transition Temperatures: K$_2$ 100 K$_1$ 104 N>200 Polymerized.

The Following Compounds were Prepared Analoguously:

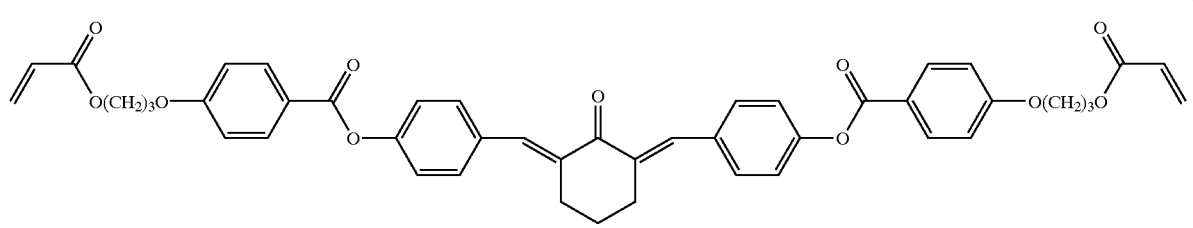

(1b)

KOH (1.06 g, 0.02 mol) and DMSO (50 ml) were stirred under N$_{2(g)}$ for 20 min. Cyclohexanone (10.6 ml,0.102 mol) was added, and the mixture was stirred for a further 25 min. 1CW01 (10.11 g, 0.46 mol) was added and left to stir for 16 hrs. The mixture was stirred at 40° C. for a further 16 h. The precipitate was removed by filtration, washed with water (3×20 ml), then recrystallised from ethanol to give a yellow crystalline solid (13.52 g, 29%). $^1$H NMR and I.R. showed expected signals.
2,6-Bis-(4-hydroxy-benzylidene)-cyclohexanone (1CW11)
1CW02 (10.0 g, 21.1 mmol), pyridinium p-toluenesulphonate (2.1 g) and methanol (300 ml) were Transition Temperatures: K 165 N 205 Polymerized.

EXAMPLE 2

Compound (2a) was Prepared According to Reaction Scheme 2 and as Described Below

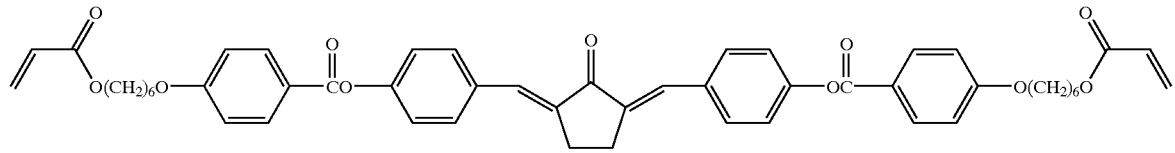

(2a)

2,5-Bis-[4-(tetrahydro-pyran-2-yloxy)-benzylidene]-cyclopentanone (1CW24)

Cyclopentanone (8.8 ml, 0.099 mol) was dissolved in ethanol (12 ml) and added to NaOH dissolved in water (25 ml) and ethanol (7 ml), and was left to stir for 25 min. This was then added to the THP protected benzaldehyde from 1CW01 (46.12 g, 0.22 mol), and the mixture was left to stir at room temperature for approximately 16 hours. A solid precipitate was isolated by vacuum filtration, washed with water (2×50 ml) and then ethanol (4×40 ml). This solid was recrystallised from ethanol to give a yellow solid (33.74 g, 74%).

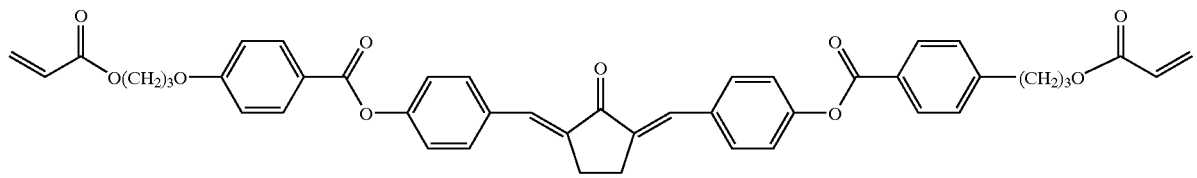

2,5-Bis-(4-hydroxy-benzylidene)-cyclopentanone (1CW24)

1CW24 (27.93 g, 0.061 mol), and pyridinium p-toluenesulphonate (2.97 g, 0.012 mol) were dissolved in methanol (200 ml) and the mixture was stirred at 35° C. for 24 h. The reaction mixture was poured into water (300 ml) and the resulting green precipitate was removed by filtration and was dried in a vacuum oven for 18 hours. This was used without further purification in the following step. Yield 17.19 g, 96%.

1CW32

HHBA-3-chloropropionate (20.32 g, 0.062 mol), 1CW29 (8.48 g, 0.029 mol), DCC (14.11 g, 0.068 mol) and DMAP (0.18 g, 0.001 mol) were stirred in DCM at room temperature for 48 h. The mixture was filtered to remove any by-products. The filtrate was washed with water (4×300 ml), dried over sodium sulphate and evaporated to dryness (26.5 g, 99%). The crude product was used without further purification in the following step.

Compound (2a) (1CW35)

Triethylamine (25 ml, 0.18 mol, 6 mol equiv.) and 1CW32 (26.5 g, 0.029 mol) were stirred in DCM (100 ml) at 35° C. for 16 h. The solution was washed with dilute acid then water (3×100 ml) and finally with brine (1×200 ml). The chlorinated layer was removed, dried over sodium sulphate and evaporated to dryness. The residue was purified by flash column chromatography (eluant=DCM:Ethyl Acetate (40:1)). $^1$H NMR and $^{13}$C NMR gave expected signals.

Transition Temperatures: K 107 N 219 I

The Following Compounds were Prepared Analoguously:

Transition temperatures:

EXAMPLE 3

Compound (3a) was Prepared According to Reaction Scheme 1 and as Described Below

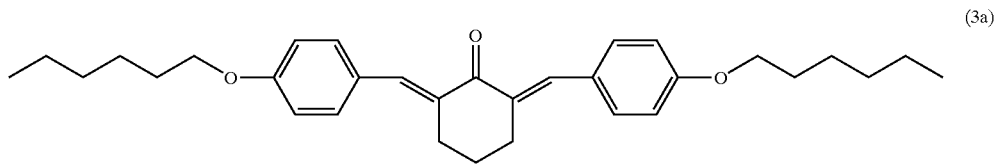

(3a)

2,6-Bis-(4-hexyloxy-benzylidene)-cyclohexanone (3a)

Cyclohexanone (2.6 ml, 0.025 mol) was dissolved in ethanol (5 ml), and was added to sodium hydroxide (0.38 g, 0.01 mol) dissolved in water (6 ml) and ethanol (2 ml) and was left to stir for 20 min. 4-Hexyloxybenzaldehyde (10 ml, 0.048 mol), dissolved in ethanol (40 ml), was added and the mixture was stirred at room temperature for 16 h. A yellow crystalline solid was isolated by vacuum filtration and was washed with cold ethanol and dried in a vacuum oven. Yield=4.32 g, 36%. $^1$H NMR and $^{13}$C NMR showed expected signals.

Transition Temperatures: K 102 N 133 I

EXAMPLE 4

Photoisomerisation of (1a) in a polymerizable Liquid Crystal Mixture

The Following Polymerizable Mixture was Prepared:

| | |
|---|---|
| Compound (1a) | 14.7% |
| Compound (A) | 75.1% |
| Compound (B) | 10.2% |

(A)

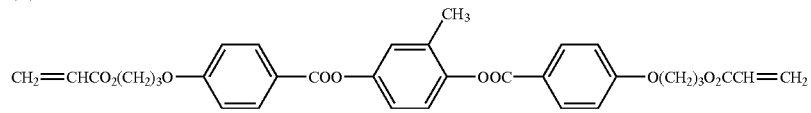

(B)

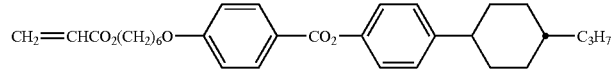

Compound (A) can be prepared as described in D. J. Broer et al., Makromol. Chem. 190, 3201–3215 (1989). Compound (B) is described in WO 98/00428.

The mixture was dissolved in 12 g of xylene and the solution was spin coated onto polyimide coated glass at 3000 rpm for 30 sec.

A homeotropically-aligned nematic phase film was produced which by super-cooling was stable to further crystallisation at room temperature for about 5 min. The film was examined between crossed polarisers on a light box, and on a polarizing microscope to confirm the nature of the alignment.

The film was exposed through a mask for 10 sec to 360 nm light from a high pressure Hg lamp which had been fitted with the appropriate band-gap filter. Examination of the film between crossed polarizers after irradiation, revealed areas of lower retardation in areas where the mask had higher transmission. An accurate image of the mask was formed on the film.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A compound of formula I

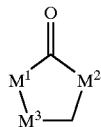

I wherein
M$^1$ and M$^2$ are independently of each other >C=CH-A$^1$-(Z$^1$-A$^2$)$_m$-R, and one of M$^1$ and M$^2$ is optionally, CH$_2$, NR$^0$, O or S,
M$^3$ is (CH$_2$)$_k$ wherein one CH$_2$ group is optionally replaced by NR$^0$, O or S,
k is 1, 2, 3 or 4,
A$^1$ and A$^2$ are independently of each other: 1,4-phenylene in which, one or more CH groups are optionally replaced by N; 1,4-cyclohexylene in which one or two non-adjacent CH$_2$ groups are optionally replaced by O and/or S; 1,3-dioxolane-4,5-diyl; 1,4-cyclohexenylene; piperidine-1,4-diyl; 1,4-bicyclo-(2,2,2)-octylene; naphthalene-2,6-diyl decahydro-naphthalene- 2,6-diyl; 1,2,3,4-tetrahydronaphthalene-2,6-diyl; or indane-2,5-diyl; all these groups optionally being mono- or polysubstituted with L,
L is halogen, CN, SCN, NO$_2$, SF$_5$ or an alkyl, alkoxy, alkylcarbonyl or alkoxycarbonyl group with 1 to 4 C atoms, wherein one or more H atoms may be substituted with F or Cl,
Z is in each case independently —O—, —S—, —CO—, —COO—, —OCO—, —CO—NR$^0$—, —NR$^0$—CO—, —CH$_2$CH$_2$—, —CF$_2$CF$_2$—, —CH$_2$CF$_2$—, —OCH$_2$—, —CH$_2$O—, —SCH$_2$—, —CH$_2$S—, —CF$_2$O—, —OCF$_2$—, —CH=CH—, —CF=CF—, —CH=CF—, —(CH$_2$)$_4$—, —CH=CH—COO—, —OCO—CH=CH—, —OOC—CHR$^{00}$—OOC—, —COO—CHR$^{00}$—COO—, —C≡C— or a single bond,
R$^0$ is H or alkyl with 1 to 4 C atoms,
R$^{00}$ is straight chain or branched alkyl or alkoxy with 1 to 8 C atoms or phenyl that is optionally mono- or polysubstituted by L,
m is 1 or 2,
R is H, halogen, NO$_2$, CN, SCN, SF$_5$, straight chain, branched or cyclic alkyl with 1 to 25 C atoms wherein one or more CH$_2$ groups are optionally replaced by —O—, —S—, —CO—, —NR$^0$—, —CH=CH—, or —C≡C—in such a manner that O and/or S atoms are not linked directly to one another, and wherein one or more H-atoms are optionally replaced by F, Cl or phenyl that is optionally mono- or polysubstituted by L, or P-(Sp-X)$_n$—,
P is a polymerizable group,
Sp is a spacer group with 1 to 20 C atoms,
X has one of the meanings of Z, and
n is 0 or 1.

2. A compound according to claim 1, wherein M$^3$ is O, S, NH, N(CH$_3$), CH$_2$, (CH$_2$)$_2$, CH$_2$O, OCH$_2$, CH$_2$S or SCH$_2$.

3. A compound according to claim 1, wherein one or both groups R denote a polymerizable group P-(Sp-X)$_n$—.

4. A compound according to claim 3, wherein P is selected from CH$_2$=CW$^1$—COO—,

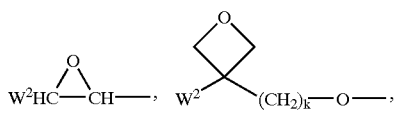

CH$_2$=CW$^2$—O—, CH$_3$—CH=CH—O—, HO—CW$^2$W$^3$—, HS—CW$^2$W$^3$—, HW$^2$N—, HO—CW$^2$W$^3$—NH—, CH$_{2=C}$W$^1$—CO—NH—, CH$_2$=CH—(COO)$_{k1}$-phe-(O)$_{k2}$—, Phe-CH=CH—, HOOC—, OCN— and W$^4$W$^5$W$^6$Si—, with W$^1$ being H, Cl, CN, phenyl or alkyl with 1 to 5 C-atoms, W$^2$ and W$^3$ being independently of each other H or alkyl with 1 to 5 C-atoms, W$^4$, W$^5$ and W$^6$ being independently of each other Cl, oxaalkyl or oxacarbonylalkyl with 1 to 5 C-atoms, Phe being 1,4-phenylene and k$_1$ and k$_2$ being independently of each other 0 or 1.

5. A liquid crystalline mixture comprising at least one compound according to claim 3.

6. A linear or crosslinked anisotropic polymer obtained by polymerizing a mixture according to claim 3.

7. A liquid crystal display comprising a polymer of claim 6.

8. A compound according to claim 1, wherein the group A$^1$-(Z$^1$-A$^2$)$_m$ is selected from a group of the following formulae and their mirror images

| | |
|---|---|
| —Phe—Z—Phe— | II-1 |
| —Phe—Z—Cyc— | II-2 |
| —Cyc—Z—Cyc— | II-3 |
| —Phe—Z—Phe—Z—Phe— | II-4 |
| —Phe—Z—Phe—Z—Cyc— | II-5 |
| —Phe—Z—Cyc—Z—Phe— | II-6 |
| —Cyc—Z—Phe—Z—Cyc— | II-7 |
| —Phe—Z—Cyc—Z—Cyc— | II-8 |
| —Cyc—Z—Cyc—Z—Cyc— | II-9 | wherein Phe is 1,4-phenylene that is optionally substituted with 1 to 4 groups L as defined in formula I, Cyc is 1,4-cyclohexylene and Z has one of the meanings of formula I.

9. A compound according to claim 1, wherein the group A$^1$-(Z$^1$-A$^2$)$_m$ is selected from groups of the following formulae and their mirror images

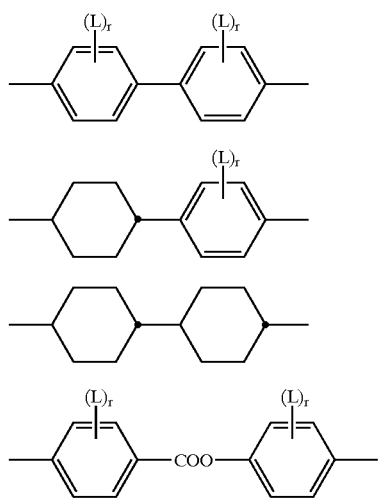

IIa

IIb

IIc

IId

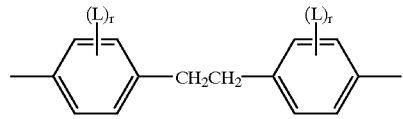

IIe

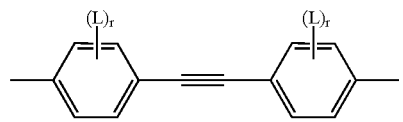

IIf

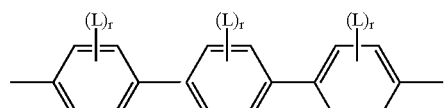

IIg

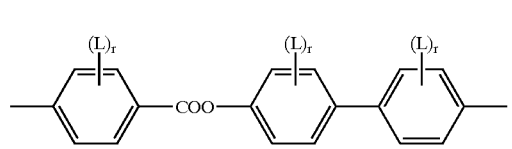

IIh

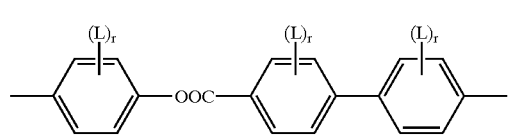

IIi

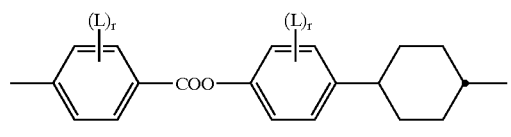

IIk

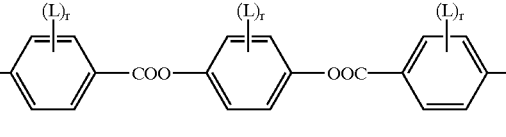

IIm

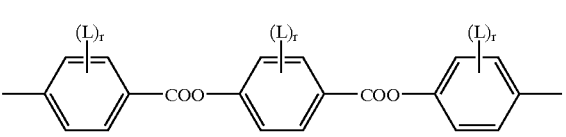

IIn

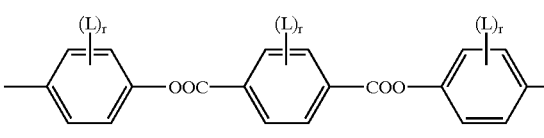

IIo

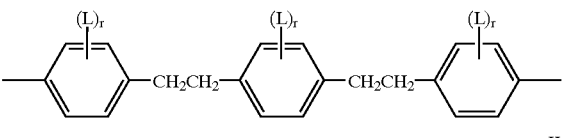

IIp

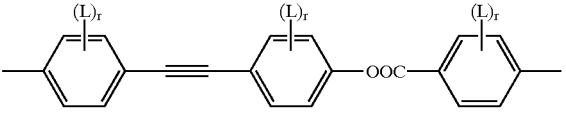

IIq

-continued

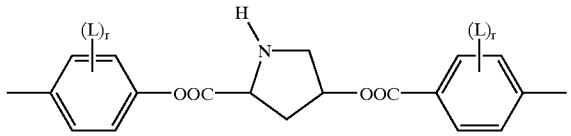
IIr wherein L has the meaning of formula I and r is 0, 1 or 2.

10. A liquid crystalline mixture comprising at least one compound according to claim 1.

11. A liquid crystalline mixture according to claim 10, comprising at least one polymerizable compound, which can be a compound of formula I or a different polymerizable compound.

12. A linear or crosslinked anisotropic polymer obtained by polymerizing a mixture according to claim 11.

13. A polymer film obtained by coating a polymerizable mixture according to claim 11, onto a substrate, aligning the mixture into uniform orientation, and polymerizing the mixture, wherein at least a part of the mixture before or during polymerization is exposed to actinic radiation of a wavelength where the photoisomerizable compound of formula I shows photoisomerization.

14. A polymer film according to claim 13, showing a pattern of at least two regions having different orientation.

15. A polymer film according to claim 13, wherein the polymerizable mixture is a nematic mixture.

16. A polymer film according to claim 13, wherein the polymerizable mixture is a chiral liquid crystalline mixture.

17. A polymer film according to claim 16, wherein the chiral liquid crystalline mixture is a cholesteric mixture.

18. A polymer film according to claim 16, wherein the chiral liquid crystalline mixture comprises a chiral compound of the formula I.

19. A polymer film according to claim 16, wherein the film comprises a pattern of discrete regions having differing reflective wavelength.

20. A retardation film, color filter or security marking comprising a polymer film of claim 19.

21. A polymer film according to claim 16, wherein the film has a pitch gradient in a direction perpendicular to the film plane.

22. A retardation film, color filter or security marking comprising a polymer film of claim 21.

23. A polymer film according to claim 13, wherein the film comprises a pattern of regions having differing birefringence or retardation.

24. A polymer film according to claim 23, wherein film is obtained from a polymerizable mixture having planar orientation.

25. A retardation film, color filter or security marking comprising a polymer film of claim 24.

26. A polymer film according to claim 23, wherein film is obtained from a polymerizable mixture having homeotropic orientation.

27. A retardation film, color filter or security marking comprising a polymer film of claim 26.

28. A retardation film, color filter or security marking comprising a polymer film of claim 23.

29. An optical device, electrooptical device, liquid crystal display, projection system, patterned film, optical element, polarizer, retardation film, compensator, color filter, holographic element polarization beam splitter, anisotropic membrane for the permeation of gases or fluids, adhesive, synthetic resin with anisotropic mechanical properties, cosmetic, pharmaceutical, UV absorber, sunscreen, diagnostic, liquid crystal pigment, decorative or security application device, nonlinear optical device, optical information storage device or dopant comprising a compound of claim 1.

30. A liquid crystal display comprising a compound according claim 1.

* * * * *

UNITED STATES PATENT AND TRADEMARK OFFICE
CERTIFICATE OF CORRECTION

PATENT NO. : 6,939,479 B2  
DATED : September 6, 2005  
INVENTOR(S) : Louise Farrand et al.

It is certified that error appears in the above-identified patent and that said Letters Patent is hereby corrected as shown below:

<u>Title page,</u>  
Item [75], Inventors, reads "Dorset (GB)" should read -- Poole (GB) --.

<u>Column 30,</u>  
Line 22, reads "diyl decahydro" should read -- diyl; decahydro --.

<u>Column 31,</u>  
Line 10, reads "$CH_{2=CW^1}$" should read -- $CH_2=CW^1$ --.  
Line 11, reads "-phe-" should read -- -Phe- --.  
Line 12, "OCN–and" should read -- OCN– and --.  
Line 22, reads "according to claim 3." should read -- according to claim 5. --.

Signed and Sealed this

Fourth Day of April, 2006

JON W. DUDAS  
*Director of the United States Patent and Trademark Office*